United States Patent [19]

Carrier

[11] Plant 5,198

[45] Feb. 28, 1984

[54] CARNATION PLANT

[76] Inventor: Leonard E. Carrier, 1911 Sheridan Rd., Encinitas, Calif. 92024

[21] Appl. No.: 431,834

[22] Filed: Sep. 30, 1982

[51] Int. Cl.[3] ..... A01H 5/00

[52] U.S. Cl. ..... Plt./73

[58] Field of Search ..... Plt./73

*Primary Examiner*—Robert E. Bagwill

*Attorney, Agent, or Firm*—James R. Cypher

[57] ABSTRACT

The present invention relates to a new and distinct cultivar of carnation plant named Big Red, which was originated by me by crossing numbered but unnamed and unpatented seedlings.

1 Drawing Figure

SUMMARY OF THE DISCLOSURE

The present invention relates to a new and distinct cultivar of Carnation Plant which was originated by me in my commercial nursery at Encinitas, Calif. by cross-breeding numbered but unnamed and unpatented seedlings.

The primary objectives of this breeding were to produce an improved carnation cultivar having improved disease resistance and production qualities, along with improved flower color, size and form, as well as less tendency of the calyx to burst and cause "splits" as the flowers open fully, which is so typical of the species botanically known as *Dianthus cadryophyllus.* These objectives were fully achieved, along with other desirable improvements, as evidenced by the following unique combination of principal characteristics which are outstanding in my new cultivar, Big Red and which distinguish it from its parents, as well as from all other carnations of which I am aware:

1. A very vigorous and free-breaking plant habit with strong and straight stems;
2. Superior resistance to soil-borne diseases such as Fusarium oxysporium and Fusarium roseum and other root-rots such as damping off, water molds, and the like.
3. Large red serrated flowers which open fully without bursting the calyx and causing "splits";
4. A distinctive and attractive red flower color which does not fade, and has no white streaks.

Asexual reproduction of my new carnation variety by side shoot cuttings rooted in peat and "Perlite" under mist, as performed under my direction and control at Encinitas, Calif., shows that the foregoing characteristics and distinctions come true and are established and transmitted through succeeding propagations.

DRAWING

The accompanying drawing illustrates typical specimens of the vegetative growth and flowers of my new carnation in different stages of development and is depicted in color as nearly true as it is reasonably possible to make the same in a color illustration of this character.

DETAILED DESCRIPTION

The following is a detailed description of my new carnation cultivar, Big Red with color terminology in accordance with Robert Ridway's Color Standards and Nomenclature (1912 edition), except where general color terms of ordinary dictionary significance are obvious.

Plant:

*Botanical classification.*—*Dianthus caryophyllus.*

*Breeding.*—Seedling. Female parent: Numbered but unnamed and unpatented seedling. Male parent: Numbered but unnamed and unpatented seedling.

*Form.*—Erect but free-branching.

*Growth.*—Strong, full, heavy stems, erect.

*Classification.*—Greenhouse type, suitable for cut flower production as a standard (one bloom per stem).

*Propagation.*—Holds its distinguishing characteristics through succeeding propagations by rooted cuttings.

*Locality where grown and observed.*—Encinitas, Calif.

*Disease resistance.*—The new cultivar has shown no evidence of fusariums or other root rots, as determined by extensive tests in high infested soils inoculated with as many strains of fungi as are locally available in the area of Encinitas, Calif.; tests conducted without chemical or steam sterilization of the soil. Soils in which the carnation plant "Sim" and others soon die.

*Temperature tolerance.*—Not hardy to cold, but grows best at temperature above 10° C.; has good resistance to hot weather in summer months of August and September at Encinitas, Calif., without hardening of growth and with only little reduction of flower size and little flower fading; no marked fading of outer flower petals even when bloom is past maturity.

*Blooming period.*—Blooms under both long and short photoperiods.

BUD: Lobes of calyx overlap in tight bud and seldom split.

*Length.*—2 cm.

*Diameter.*—2.5 cm.

*Color.*—Spectrum Red, Plate 1, 1 Red.

Peduncle:

*Strength.*—Strong.

*Color.*—M. Bottle Green Plate XIX, 37′ GB-G.

Bloom:

*Size.*—8.0 cm. diameter, depth 3.0 cm.

*Stem.*—Consist of 9 nodes: Length is 60 cm. Diameter is 0.9 cm. at base and about 0.4 cm. at base of calyx. Color is M. Bottle Green Plate XIX, 37′ GB-G.

*Petalage.*—From 80 to 90 petals. Outer petals are about 4.0 cm. wide and about 5.0 cm. long. Center petals are about 2.0 cm. wide and about 4.0 cm. long.

*Color.*—The center of flower, outer petals, base of petals, inside of petals and reverse of petals are all Spectrum red plate 1, 1 Red.

*General tonality.*—Uniform red with no white streaks.

*Petals.*—Texture is firm. Form: Outer petals nearly semi-circular, roughly uniform serrations 3 large and 8 small serrations to cm. Opening: Normal with minimum of split calyx's.

*Fragrance.*—No distinctive fragrance.

Foliage:

*Form.*—Flat curled.

*Size.*—1 cm. wide and 13 cm. long.

*Quantity.*—Two leaves per node, with nodes spaced about 9 cm. apart.

*Color.*—The upper and under sides of both young and mature plants are all M Bottle Green plate XIX, 37′ GB-G.

*Texture.*—Smooth.

I claim:

1. A new and distinct cultivar of carnation plant named Big Red substantially as herein shown and described, characterized particularly as to novelty by the unique combination of a very vigorous and free-breaking plant habit, and strong and straight stems; superior resistance to soil-borne diseases such as Fusarium oxysporium and Fusarium roseum and other root-rots such as damping off, water molds, and the like; large serrated flowers which open fully without bursting the calyx and causing "splits"; a distinctive and attractive red flower color which does not fade and has no white streaks; and good heat tolerance which is superior to that of the parent lines and the so-called "Sim".

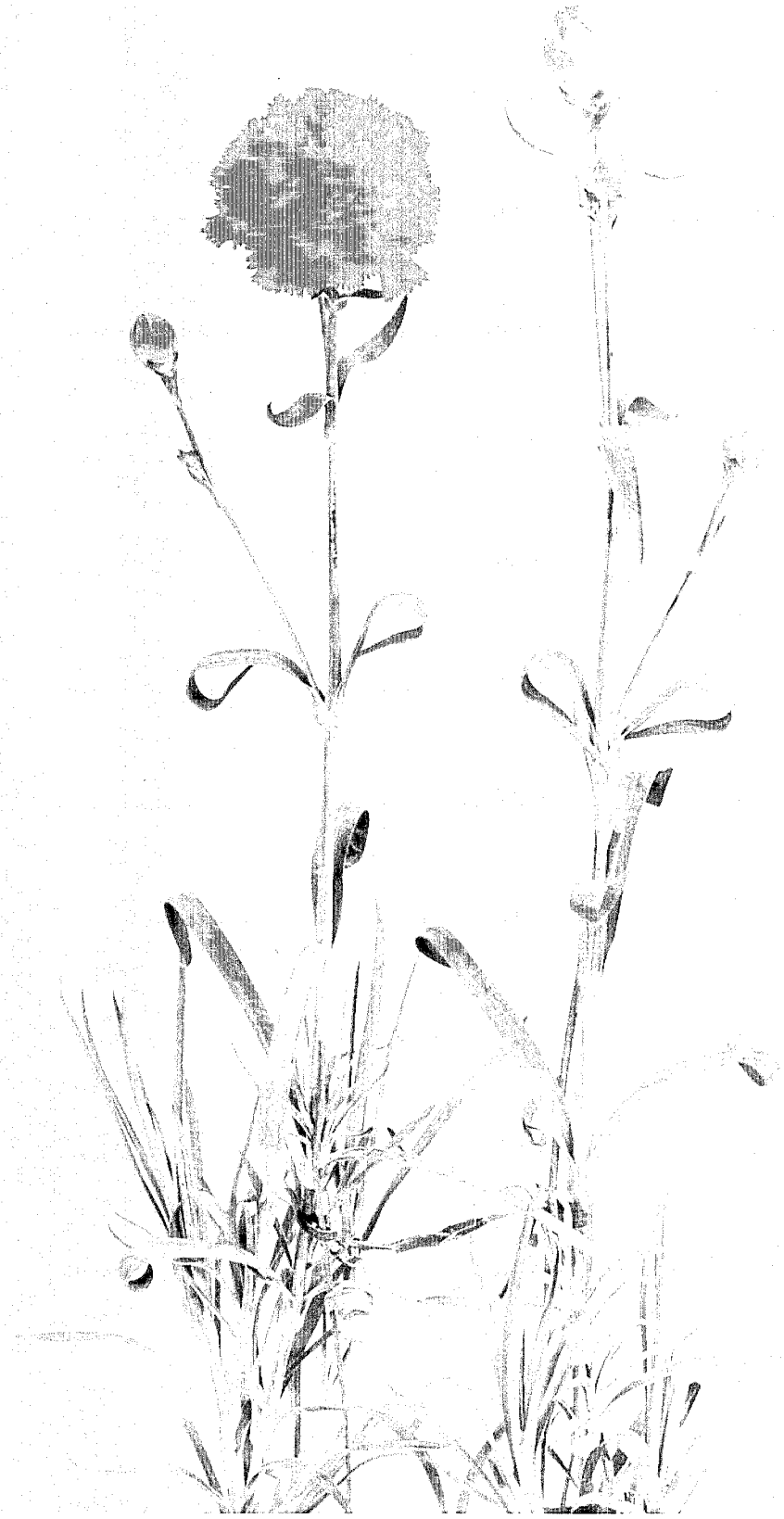

* * * * *